US010349916B2

(12) United States Patent
Tashiro (10) Patent No.: US 10,349,916 B2
(45) Date of Patent: Jul. 16, 2019

(54) ULTRASOUND DIAGNOSTIC APPARATUS AND ULTRASOUND IMAGE DISPLAY METHOD (71) Applicant: FUJIFILM CORPORATION, Tokyo (JP)

(72) Inventor: Rika Tashiro, Ashigara-kami-gun (JP)

(73) Assignee: FUJIFILM CORPORATION, Tokyo (JP)

(*) Notice: Subject to any disclaimer, the term of this patent is extended or adjusted under 35 U.S.C. 154(b) by 1478 days.

(21) Appl. No.: 13/866,998

(22) Filed: Apr. 19, 2013

(65) Prior Publication Data
US 2013/0281834 A1 Oct. 24, 2013

(30) Foreign Application Priority Data

Apr. 23, 2012 (JP) ................................ 2012-097563

(51) Int. Cl.
A61B 8/00 (2006.01)
A61B 8/08 (2006.01)
A61B 8/14 (2006.01)

(52) U.S. Cl.
CPC ............ *A61B 8/0841* (2013.01); *A61B 8/145* (2013.01); *A61B 8/463* (2013.01); *A61B 8/5292* (2013.01); *A61B 8/54* (2013.01)

(58) Field of Classification Search
CPC .................. A61B 8/0841; A61B 8/463; A61B 2017/3413
USPC ........................................................ 600/424
See application file for complete search history.

(56) References Cited

U.S. PATENT DOCUMENTS 5,016,642 A * 5/1991 Dukes ................. G01S 7/52055
600/443
2005/0251037 A1 * 11/2005 Watanabe ................ A61B 8/08
600/437
2007/0010743 A1 * 1/2007 Arai ......................... A61B 8/13
600/443

(Continued)

FOREIGN PATENT DOCUMENTS

JP H 08-117223 A 5/1996
JP H 09-028712 A 2/1997

(Continued)

OTHER PUBLICATIONS

Japanese Office Action dated Sep. 1, 2015 with a partial English translation thereof.

(Continued)

*Primary Examiner* — Rajeev P Siripurapu
(74) *Attorney, Agent, or Firm* — McGinn I.P. Law Group, PLLC.

(57) ABSTRACT

An ultrasound diagnostic apparatus comprises an operating unit for inputting an instruction from an operator; and a controller for eliminating at least a part of the puncture guide line, which has been displayed so as to be superimposed on the ultrasound image, when an instruction for non-display of the puncture guide line is given through the operating unit during the freeze operation, and automatically returning the eliminated puncture guide line and displaying the eliminated puncture guide line so as to be superimposed on the real-time ultrasound image at the time of returning from the freeze operation to the live operation.

12 Claims, 7 Drawing Sheets (56) References Cited

U.S. PATENT DOCUMENTS

2008/0246724 A1\* 10/2008 Pan ..................... G01S 7/52073
                                                              345/157
2010/0298704 A1\* 11/2010 Pelissier ................. A61B 5/06
                                                              600/443

FOREIGN PATENT DOCUMENTS

JP          2000-126186 A        5/2000
JP          2007-195867 A        8/2007

OTHER PUBLICATIONS

Chinese Office Action dated Jan. 25, 2016 with an English translation.

\* cited by examiner

PRIOR ART

FIG. 8B

PRIOR ART

ULTRASOUND DIAGNOSTIC APPARATUS AND ULTRASOUND IMAGE DISPLAY METHOD

BACKGROUND OF THE INVENTION

This invention relates to an ultrasound diagnostic apparatus and an ultrasound image display method. More specifically, this invention relates to an ultrasound diagnostic apparatus and an ultrasound image display method to display the puncture guide line so as to be superimposed on an ultrasound image.

In the medical field, an ultrasound diagnostic apparatus using an ultrasound image has been put into practical use. Generally, this kind of ultrasound diagnostic apparatus includes an ultrasound probe with an integrated transducer array and the apparatus body connected to the ultrasound probe, and generates an ultrasound image by transmitting an ultrasonic wave toward a subject from the ultrasound probe, receiving an ultrasonic echo from the subject using the ultrasound probe, and processing the reception signal electrically in the apparatus body.

In recent years, the ultrasound diagnostic apparatus is also used when inserting the puncture needle into the subject to sample specific body tissue and performing a biopsy or the like. In this ultrasound diagnostic apparatus, the puncture needle is moved to target body tissue while checking the movement of the puncture needle within the subject through an ultrasound image displayed on a monitor by transmitting an ultrasound beam toward the subject from the ultrasound probe and receiving an ultrasound beam reflected from the subject using the ultrasound probe. In addition, a puncture guide line for guiding the puncture needle from the surface of the subject to the target body tissue is displayed on the monitor so as to be superimposed on the ultrasound image, so that the arrival of the puncture needle at the target body tissue can be supported by the puncture guide line. However, since the puncture needle is embedded in the surrounding body tissue in the ultrasound image, it has been difficult to check the position clearly.

Therefore, as a technique for clearly displaying the position of the puncture needle in an ultrasound image, for example, as disclosed in JP 2007-195867 A, dividing an ultrasound image into a region including a puncture guide line and the other region and performing image processing, such as narrowing a dynamic range, on the region including the puncture guide line has been proposed. In the ultrasound diagnostic apparatus disclosed in JP 2007-195867 A, since the puncture needle is emphasized by performing image processing on the region including the puncture guide line in the ultrasound image, it is possible to make the position of the puncture needle clear.

Figure 8A:
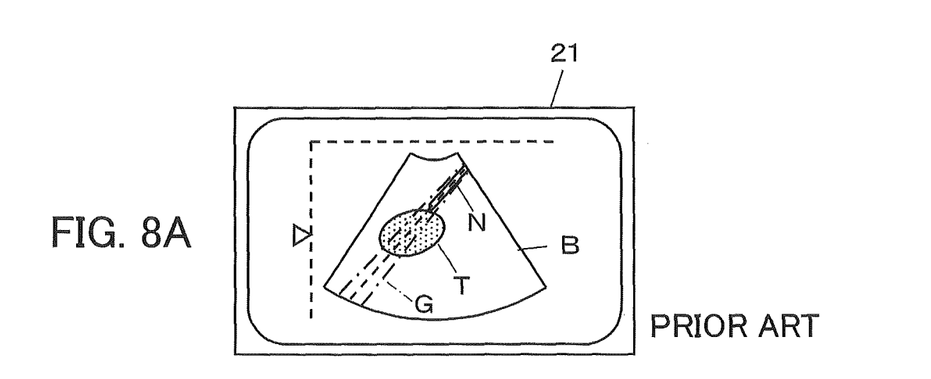
FIGS. 8A and 8B are diagrams showing a state of an ultrasound image displayed on a monitor at the time of switching from the freeze operation to the live operation in a conventional example.
Figure 8B:
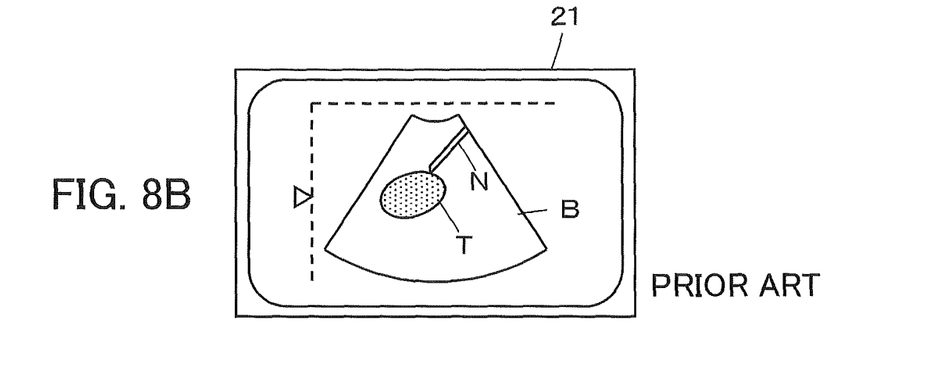

In addition, since the puncture needle or the target body tissue overlaps the puncture guide line, there has been a problem in that it is difficult to check these positions in detail. Therefore, an ultrasound diagnostic apparatus has been developed that can check the positions of a puncture needle N and body tissue T in detail by freezing a real-time ultrasound image B, which is displayed on a monitor 21, first as shown in FIG. 8A and then not displaying a puncture guide line G, which is displayed so as to be superimposed on the ultrasound image, as shown in FIG. 8B.

However, at the time of returning from the freeze operation to the live operation to display the real-time ultrasound image B in order to continue the puncture, an operation to display the puncture guide line G should be performed again since the puncture guide line G is not displayed. Accordingly, it has been difficult to perform smooth switching from the freeze operation to the live operation to continue the puncture. For this reason, when the live operation and the freeze operation are switched many times while maintaining a puncture state, for example, when performing puncture by changing the angle of the puncture needle N little by little while performing switching between the freeze operation and the live operation, an operation to display the puncture guide line G should be performed at each time of returning to the live operation. This may disturb the puncture.

SUMMARY OF THE INVENTION

This invention has been made to solve the problems described above, and it is an object of this invention to provide an ultrasound diagnostic apparatus and an ultrasound image display method enabling smooth switching from freeze operation to live operation to perform puncture.

An ultrasound diagnostic apparatus according to the present invention comprises: a vibrator array; a transmission circuit that transmits an ultrasound beam toward a subject from the vibrator array; a reception circuit that generates reception data by processing a reception signal output from the vibrator array that has received an ultrasonic echo from the subject; an image producer that generates an ultrasound image on the basis of the reception data obtained by the reception circuit; a monitor that displays an ultrasound image generated by the image producer; a puncture needle to be inserted into the subject; an operating unit used to input an instruction from an operator; and a controller that selects either a live operation to display a puncture guide line so as to be superimposed on a real-time ultrasound image displayed on the monitor or a freeze operation to reproduce an ultrasound image of a predetermined frame on the monitor according to an operation of the operating unit by the operator, eliminates at least a part of the puncture guide line, which has been displayed so as to be superimposed on the ultrasound image, when an instruction for non-display of the puncture guide line is given through the operating unit during the freeze operation, and automatically returns the eliminated puncture guide line and displays the eliminated puncture guide line so as to be superimposed on the real-time ultrasound image at the time of returning from the freeze operation to the live operation.

An ultrasound image display method according to the present invention comprises: inputting an instruction from the operator; and eliminating at least a part of the puncture guide line, which has been displayed so as to be superimposed on the ultrasound image, when an instruction for non-display of the puncture guide line is given from the operator during the freeze operation, and automatically returning the eliminated puncture guide line and displaying the eliminated puncture guide line so as to be superimposed on the real-time ultrasound image at the time of returning from the freeze operation to the live operation.

According to this invention, at the time of returning from the freeze operation to the live operation, the eliminated puncture guide line is automatically returned and displayed so as to be superimposed on the real-time ultrasound image. Therefore, it is possible to perform smooth switching from the freeze operation to the live operation to perform puncture.

DETAILED DESCRIPTION OF THE INVENTION

Hereinafter, embodiments of this invention will be described with reference to the accompanying drawings.

First Embodiment

Figure 1:
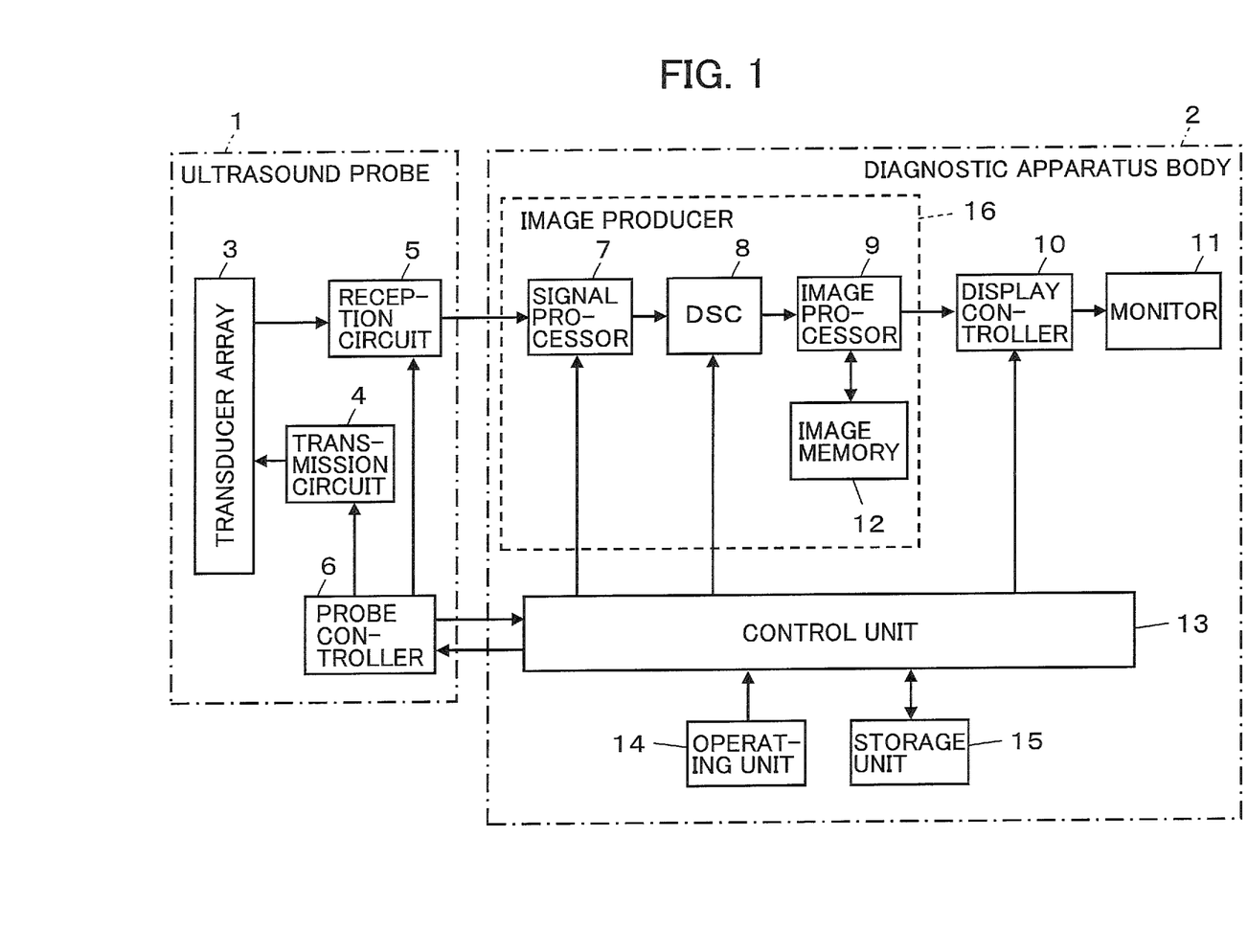
FIG. 1 is a block diagram showing the configuration of an ultrasound diagnostic apparatus according to a first embodiment of this invention.

FIG. 1 shows the configuration of an ultrasound diagnostic apparatus according to a first embodiment of this invention. The ultrasound diagnostic apparatus includes an ultrasound probe 1 and a diagnostic apparatus body 2 connected to the ultrasound probe 1.

The ultrasound probe 1 includes a transducer array 3 to transmit and receive an ultrasonic wave, and a transmission circuit 4 and a reception circuit 5 are connected to the transducer array 3. In addition, a probe controller 6 is connected to the transmission circuit 4 and the reception circuit 5.

The diagnostic apparatus body 2 includes a signal processor 7 connected to the reception circuit 5 of the ultrasound probe 1, and a DSC (Digital Scan Converter) 8, an image processor 9, a display controller 10, and a monitor 11 are sequentially connected to the signal processor 7. In addition, an image memory 12 is connected to the image processor 9.

In addition, a control unit 13 is connected to the signal processor 7, the DSC 8, and the display controller 10. In addition, an operating unit 14 and a storage unit 15 are connected to the control unit 13. In addition, the probe controller 6 of the ultrasound probe 1 and the control unit 13 of the diagnostic apparatus body 2 are connected to each other.

The transducer array 3 of the ultrasound probe 1 has a plurality of ultrasound transducers arrayed in a one-dimensional or two-dimensional manner. According to a driving signal supplied from the transmission circuit 4, each of the ultrasound transducers transmits an ultrasonic wave and also receives an ultrasonic echo from the subject and outputs the reception signal. Each ultrasound transducer is configured by a vibrator in which electrodes are formed at both ends of the piezoelectric body formed of piezoelectric ceramic represented by PZT (lead zirconate titanate), a polymer piezoelectric element represented by PVDF (polyvinylidene fluoride), piezoelectric single crystal represented by PMN-PT (lead magnesium niobate-lead titanate solid solution), or the like, for example.

When a pulsed or continuous-wave voltage is applied to the electrodes of the vibrator, the piezoelectric body expands and contracts to generate pulsed or continuous-wave ultrasonic waves from each vibrator. By combination of these ultrasonic waves, an ultrasound beam is formed. In addition, each vibrator expands and contracts by receiving the ultrasonic waves that propagate, thereby generating electric signals. These electric signals are output as reception signals of the ultrasonic waves.

The transmission circuit 4 includes a plurality of pulsers, for example. The transmission circuit 4 adjusts the amount of delay of each driving signal on the basis of the transmission delay pattern, which is selected according to the control signal from the probe controller 6, so that ultrasonic waves transmitted from the plurality of ultrasound transducers of the transducer array 3 form an ultrasound beam, and supplies the adjusted signals to the plurality of ultrasound transducers.

The reception circuit 5 performs amplification and A/D conversion of the reception signals transmitted from the ultrasound transducers of the transducer array 3 and then adds the reception signals after delaying each reception signal according to the reception delay pattern, which is selected according to the control signal from the probe controller 6, thereby performing reception focusing processing. Through this reception focusing processing, reception data (sound ray signal) with narrowed focus of the ultrasonic echo is generated.

The probe controller 6 controls each unit of the ultrasound probe 1 on the basis of various control signals transmitted from the control unit 13 of the diagnostic apparatus body 2.

The signal processor 7 of the diagnostic apparatus body 2 generates a B-mode image signal, which is tomographic image information regarding tissue within the subject, by performing correction of attenuation based on the distance, which depends on the depth of the reflection position of the ultrasonic wave, for the reception data generated by the reception circuit 5 of the ultrasound probe 1 and then performing envelope detection processing.

The DSC 8 converts the B-mode image signal generated by the signal processor 7 into an image signal according to the normal television signal scanning method (raster conversion).

The image processor 9 performs various kinds of required image processing, such as gradation processing, on the B-mode image signal input from the DSC 8 and then outputs the B-mode image signal to the display controller 10 or stores the B-mode image signal in the image memory 12. Accordingly, real-time ultrasound images are sequentially stored in the image memory 12. In addition, an ultrasound image of a predetermined frame selected by the operator, among the ultrasound images sequentially stored, can also be newly stored in the image memory 12.

An image producer 16 is formed by the signal processor 7, the DSC 8, the image processor 9, and the image memory 12.

The display controller 10 displays an ultrasound image on the monitor 11 on the basis of the B-mode image signal subjected to image processing by the image processor 9.

The monitor 11 includes a display device, such as an LCD, for example, and displays an ultrasound image under the control of the display controller 10.

The control unit 13 controls each unit of the ultrasound diagnostic apparatus on the basis of the instruction input from the operating unit 14 by the operator. In addition, the control unit 13 displays a puncture guide line, which guides the puncture needle inserted into the subject to the target body tissue, so as to be superimposed on the ultrasound image displayed on the monitor 11.

The operating unit 14 is for inputting an instruction from the operator, and may be formed by a keyboard, a mouse, a track ball, a touch panel, and the like. For example, the operating unit 14 may include an operation selection button for selecting either a live operation to display a real-time ultrasound image or a freeze operation to reproduce an ultrasound image of a predetermined frame, a guide line elimination button for eliminating the puncture guide line displayed so as to be superimposed on an ultrasound image, a storage button for selecting an ultrasound image of a predetermined frame and storing it in the image memory 12, and the like.

The storage unit 15 stores an operation program and the like, and recording media, such as a hard disk, a flexible disk, an MO, an MT, a RAM, a CD-ROM, a DVD-ROM, an SD card, a CF card, and a USB memory, or a server may be used.

In addition, although the signal processor 7, the DSC 8, the image processor 9, the display controller 10, and the control unit 13 are realized by a CPU and an operation program causing the CPU to execute various kinds of processing, they may also be formed using digital circuits.

Figure 2:
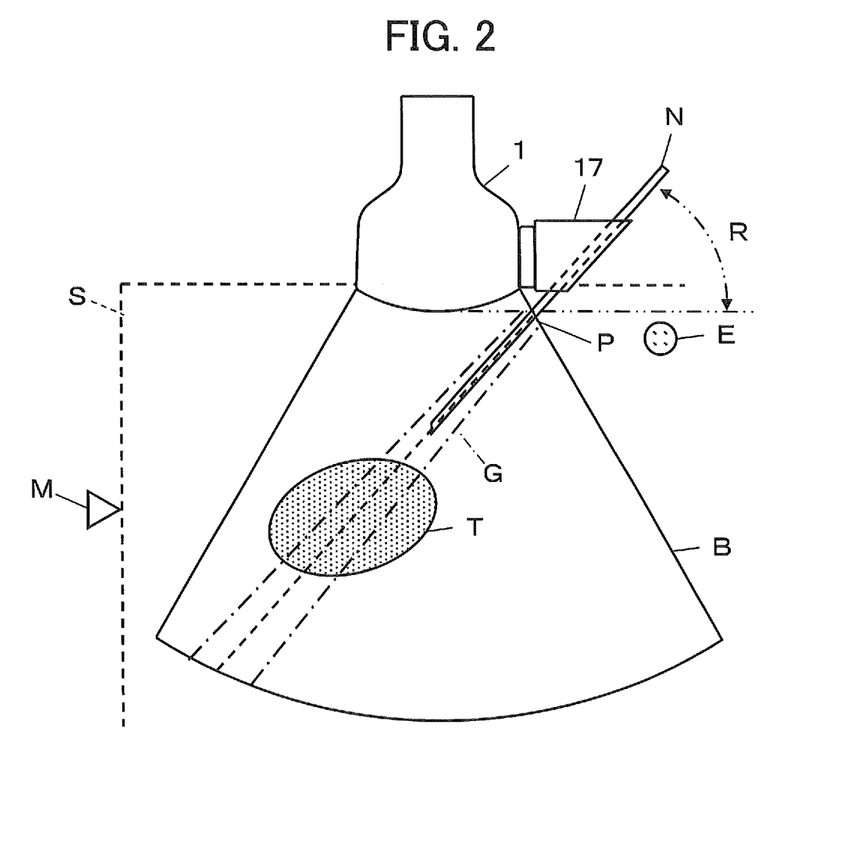
FIG. 2 is a diagram showing an ultrasound image displayed on a monitor.

FIG. 2 illustrates an ultrasound image displayed on the monitor 11.

On the monitor 11, the ultrasound image B obtained by transmitting and receiving an ultrasonic wave from the ultrasound probe 1 is displayed, and the puncture guide line G is also displayed so as to be superimposed on the ultrasound image B.

The puncture guide line G extends to specific body tissue T within the subject, and is intended to be a guide when inserting the puncture needle N into the subject. The position or the angle of the puncture guide line G is set in advance, for example, according to a puncture needle attachment 17 attached to the ultrasound probe 1. The puncture needle attachment 17 is intended to fix the insertion position P or the insertion angle R of the puncture needle N with respect to the ultrasound probe 1, and is appropriately selected and used according to the depth position or the like of the specific body tissue T within the subject. Since the insertion direction from the insertion position P to the body tissue T is determined in this manner by the puncture needle attachment 17, the position or angle of the puncture guide line G can be set in advance according to the puncture needle attachment 17.

In addition, a probe direction mark E indicating the direction of the ultrasound probe 1 is displayed on the monitor 11. In addition, a scale S indicating the depth and width of the ultrasound image B is displayed on the monitor 11, and a focus indicator M indicating the focal depth is also displayed on the monitor 11.

Next, the operation in the first embodiment will be described.

First, the ultrasound probe 1 is placed at a predetermined position of the surface of the subject, and the operator operates the operation selection button of the operating unit 14 to select a live operation to display the puncture guide line G so as to be superimposed on the real-time ultrasound image B displayed on the monitor 11.

When the live operation is selected by the operator, an ultrasound beam is transmitted from the transducer array 3 of the ultrasound probe 1 placed on the surface of the subject, and a reception signal is output to the reception circuit 5 from the transducer array 3 that has received an ultrasonic echo from the inside of the subject. As a result, reception data is generated. Then, the reception data is output from the reception circuit 5 to the image producer 16 of the diagnostic apparatus body 2, and an ultrasound image is generated. The ultrasound image generated in this manner is sequentially stored in the image memory 12 of the image producer 16 and is also displayed on the monitor 11 by the display controller 10.

On the other hand, as shown in FIG. 2, the puncture needle attachment 17 according to the position of the specific body tissue T within the subject is attached to the ultrasound probe 1. In addition, the operator inputs the type of the puncture needle attachment 17, which is attached to the ultrasound probe 1, to the control unit 13 of the diagnostic apparatus body 2 through the operating unit 14. In the control unit 13, the puncture guide line G for guiding the puncture needle N from the insertion position P to the body tissue T is set in advance according to the puncture needle attachment 17, and the puncture guide line G extending from the insertion position P to the body tissue T corresponding to the puncture needle attachment 17 is displayed so as to be superimposed on the ultrasound image B.

Figure 3A:
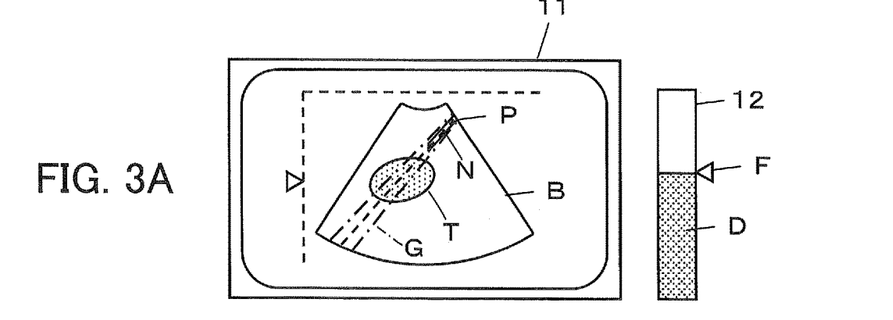
FIGS. 3A to 3D are diagrams each showing a state of an ultrasound image displayed on a monitor at the time of switching to the live operation or the freeze operation.

Therefore, as shown in FIG. 3A, the puncture guide line G is displayed on the monitor 11 so as to be superimposed on the real-time ultrasound image B. In addition, ultrasound image data D is sequentially stored in the image memory 12, and a newest ultrasound image stored in the image memory 12 is displayed on the monitor 11 so that a display position mark F indicating the storage location of the ultrasound image data D displayed on the monitor 11 is displayed.

Then, the operator inserts the puncture needle N into the subject along the puncture needle attachment 17 attached to the ultrasound probe 1, and moves the puncture needle N into the subject according to the puncture guide line G displayed on the monitor 11. By moving the puncture needle N according to the puncture guide line G in this manner, the puncture needle N can easily reach the body tissue T. In this case, the operator selects a freeze operation with the operation selection button of the operating unit 14, for example, in order to store a state where the puncture needle N has reached the specific body tissue T as an image.

Figure 3B:
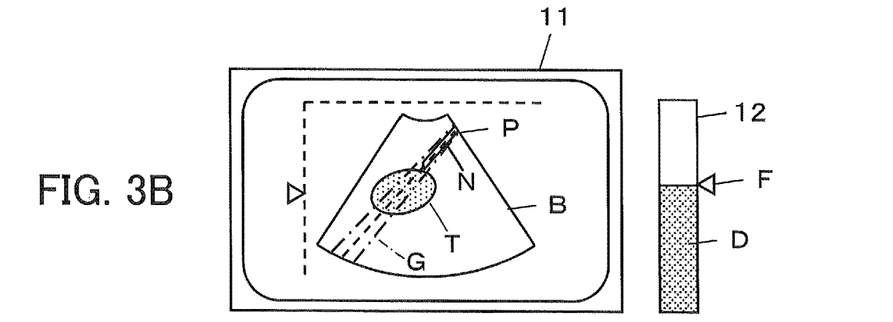

When the instruction of freeze operation from the operator is input to the control unit 13 through the operating unit 14, the control unit 13 controls the display controller 10 so that the ultrasound image B of the frame at the timing when the freeze operation has been selected is displayed on the monitor 11 with the puncture guide line, as shown in FIG. 3B.

Figure 3C:
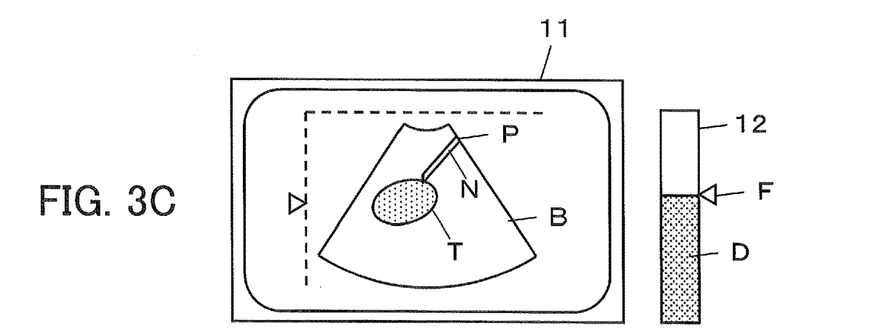

In addition, when the puncture site of the specific body tissue T punctured by the puncture needle N is superimposed on the puncture guide line G, the operator operates the guide line elimination button of the operating unit 14. As a result, as shown in FIG. 3C, the puncture guide line G displayed so as to be superimposed on the ultrasound image B is eliminated and only the ultrasound image B is displayed. In this case, since a portion superimposed on the puncture guide line G can be clearly displayed, the operator can easily check things that have been difficult to see conventionally because the portion is embedded in the puncture guide line G, for example, the insertion direction of the puncture needle N with respect to the body tissue T. In addition, for example, when medicine for treatment is administered to the body tissue T through the puncture needle N, the spread of the medicine administered through the puncture needle N, which has been difficult to see conventionally due to the puncture guide line G, can be easily checked in the present invention.

In addition, when the operator wants to store the ultrasound image B of the frame checked during the freeze operation, the ultrasound image B can be newly stored in the image memory 12 in a state where the puncture guide line G has been eliminated by operating the storage button of the operating unit 14. Accordingly, since the ultrasound image B of an important frame in a series of puncture can be stored in a state where the puncture guide line G has been eliminated, a state of the arrival of the puncture needle N at the body tissue T or the treatment status at that time can be checked using only the ultrasound image B after the end of ultrasound diagnosis or the like.

Figure 3D:
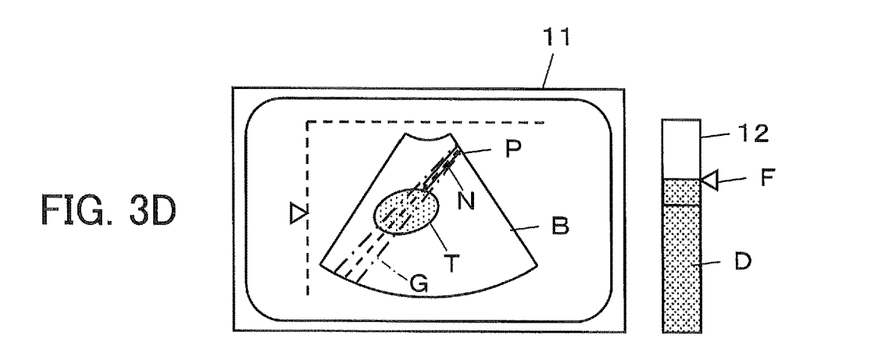

When continuing the puncture after storing the puncture state as described above, the operator operates the operation selection button of the operating unit 14 for returning from the freeze operation to the live operation. That is, when the instruction of live operation from the operator is input to the control unit 13 through the operating unit 14, the control unit 13 controls the display controller 10 so that the real-time ultrasound image B is displayed on the monitor 11 and the eliminated puncture guide line G is also automatically returned and displayed on the monitor 11 so as to be superimposed on the ultrasound image B, as shown in FIG. 3D.

Thus, at the time of returning from the freeze operation to the live operation, the eliminated puncture guide line G is automatically returned. Accordingly, the operator can continue the puncture again according to the puncture guide line G without being disturbed by the display operation of the puncture guide line G. For example, even when switching between the live operation and the freeze operation is repeated many times, the puncture guide line G is automatically displayed at each time of returning to the live operation. Therefore, since returning to the original live operation is possible with a small number of steps, it is possible to perform smooth switching from the freeze operation to the live operation to continue the puncture.

Figure 4:
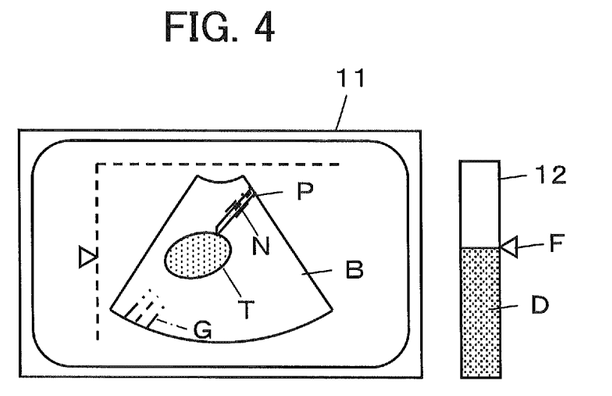
FIG. 4 is a diagram showing a puncture guide line displayed in a modification of the first embodiment.

In addition, in the embodiment described above, when non-display of the puncture guide line G is instructed from the operating unit 14 during the freeze operation, the entire puncture guide line G that has been displayed so as to be superimposed on the ultrasound image B is eliminated. However, since a part of the puncture guide line G may be eliminated so that the puncture needle N or the body tissue T can be checked, this invention is not limited to those described above. For example, as shown in FIG. 4, when non-display of the puncture guide line G is instructed from the operating unit 14 during the freeze operation, only a middle portion of the puncture guide line G displayed so as to be superimposed on the ultrasound image B can be eliminated.

In this case, the body tissue T and the puncture needle N located in the middle portion of the ultrasound image B are clearly displayed, and the information from the puncture guide line G, such as the insertion direction of the puncture needle N, can also be acquired. The ultrasound image B is stored in the image memory 12, for example, so that the operator checks the positions of the puncture needle N and the body tissue T and the like in detail.

In addition, the control unit 13 may automatically change the display color of the puncture guide line G, which has been displayed so as to be superimposed on the ultrasound image B, when the operator performs switching from the live operation to the freeze operation. In this case, the operator can determine the current operation just by looking at the display color of the puncture guide line G displayed on the monitor 11. Accordingly, it is possible to prevent an erroneous operation, such as inserting the puncture needle N during the freeze operation.

Second Embodiment

In the first embodiment, when the operator performs switching from the live operation to the freeze operation using the operation selection button of the operating unit 14, switching timing may be shifted. For example, when the operator instructs another person to perform switching to the freeze operation, shift occurs before the operating unit 14 is actually operated after the operator sends the instruction, or shift occurs before the operating unit 14 is actually operated after the operator sees an ultrasound image. When a desired ultrasound image B is not displayed on the monitor 11 due to switching timing shift as described above, the desired ultrasound image B can be displayed on the monitor 11 by adjusting the position of the display position mark F shown in FIG. 3B, for example.

In addition, the desired ultrasound image B can also be automatically displayed on the monitor 11 by setting a time C of the switching timing shift in the control unit 13 in advance.

Figure 5A:
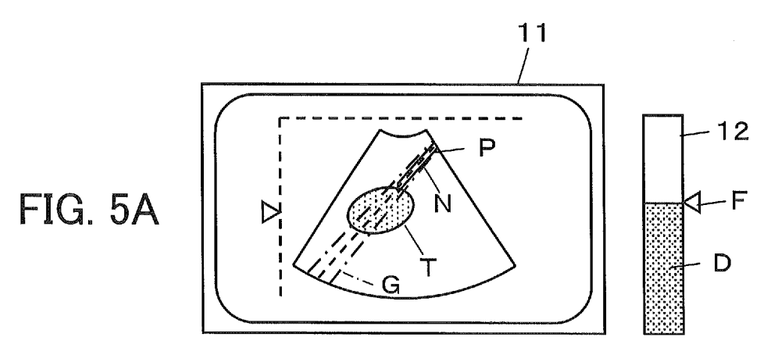
FIGS. 5A and 5B are diagrams showing a state of an ultrasound image displayed on a monitor at the time of switching from the live operation to the freeze operation in a second embodiment.
Figure 5B:
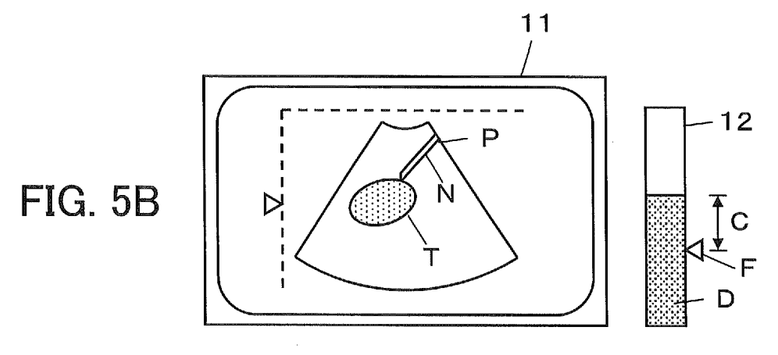

For example, the operator performs switching from the live operation to the freeze operation using the operation selection button of the operating unit 14 as shown in FIG. 5A, and then the operator eliminates the puncture guide line G displayed so as to be superimposed on the ultrasound image B using the guide line elimination button of the operating unit 14 as shown in FIG. 5B. In this case, the control unit 13 may reproduce an ultrasound image of a frame, which is earlier than the timing of switching to the freeze operation by the predetermined time C, on the monitor 11 in consideration of the timing shift when the operator performs switching to the freeze operation.

Figure 6A:
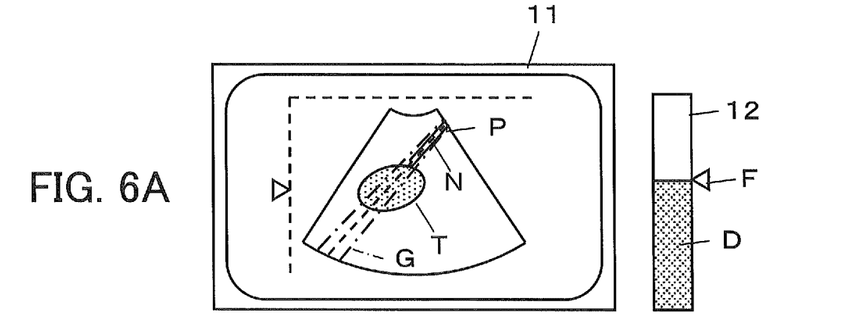
FIGS. 6A and 6B are diagrams showing a state of an ultrasound image displayed on a monitor at the time of switching from the live operation to the freeze operation in a modification of the second embodiment.
Figure 6B:
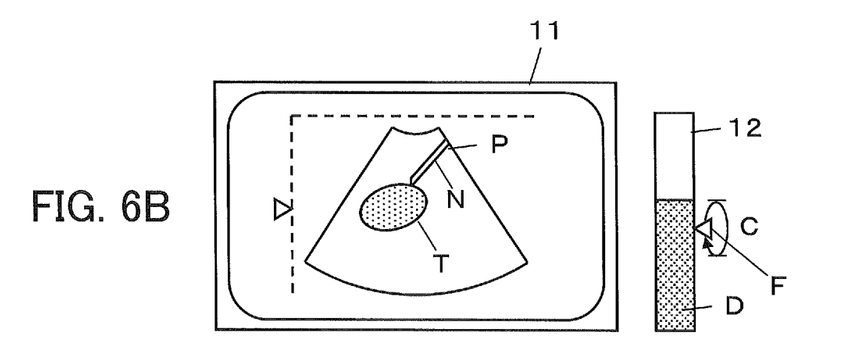

In addition, after switching from the live operation to the freeze operation by the instruction from the operating unit 14 as shown in FIG. 6A, the puncture guide line G is eliminated by the instruction from the operating unit 14 as shown in FIG. 6B. In this case, the control unit 13 may perform loop reproduction of ultrasound images of a plurality of frames, which are located in a range of the predetermined time C from the timing of switching to the freeze operation, in consideration of the timing shift when the operator performs switching to the freeze operation. This makes it easier for the operator to select a desired ultrasound image from a series of loop-reproduced puncture flow.

In addition, when injecting medicine through the puncture needle N in order to treat the body tissue T, the operator can check the spread state of medicine again by storing the spread state of medicine injected into the body tissue T as a moving image for about 60 seconds, for example, and then returning by the medicine injection time (60 seconds) in consideration of timing shift of switching to the freeze operation and performing loop reproduction of 60 seconds of medicine injection from there. In addition, the moving image of medicine injection may be stored as it is.

Thus, it is possible to reduce the effort to search for a desired ultrasound image from the ultrasound image data stored in the image memory 12 by performing display taking into consideration the shift of the timing at which the operator operates the operating unit 14.

Figure 7A:
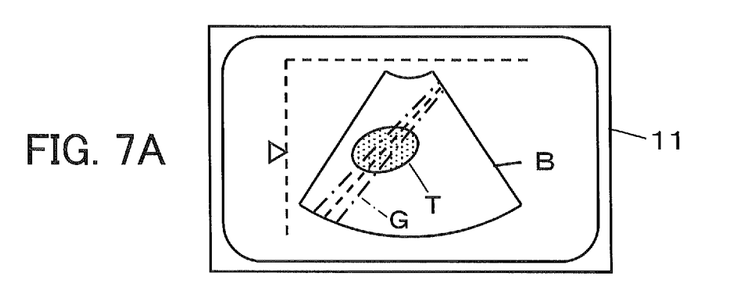
FIGS. 7A to 7C are diagrams showing the puncture guide lines displayed in modifications of the first and second embodiments.
Figure 7B:
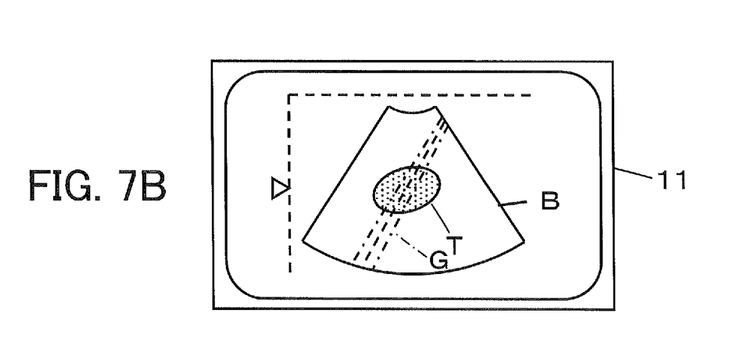
Figure 7C:
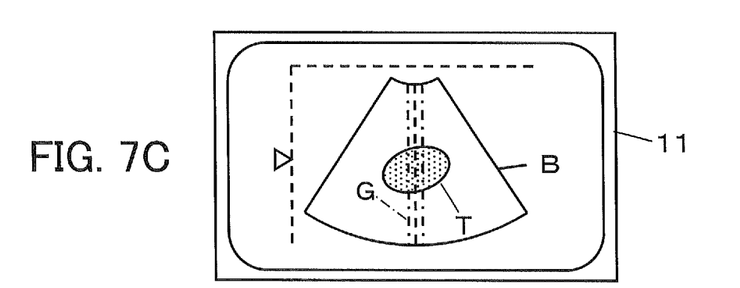

In addition, in the first and second embodiments, it is preferable that the insertion angle R of the puncture needle N inserted into the subject be set in advance according to the type of target body tissue T or the like. For example, the insertion angle R of the puncture needle N can be set to 48°, 60°, and 90°. When the insertion angle R is 48°, the puncture guide line G is displayed so as to be superimposed on the ultrasound image B at the angle of 48°, as shown in FIG. 7A. In addition, when the insertion angle R is 60°, the puncture guide line G is displayed so as to be superimposed on the ultrasound image B at the angle of 60°, as shown in FIG. 7B. In addition, when the insertion angle R is 90°, the puncture guide line G is displayed so as to be superimposed on the ultrasound image B at the angle of 90°, as shown in FIG. 7C.

By setting the insertion angle R of the puncture needle N in advance according to the type of body tissue T as described above, it is possible to reduce the effort when the operator sets the insertion angle R or the puncture guide line G.

In addition, the insertion angle R, the insertion position P, and the like of the puncture needle N can also be set arbitrarily by the operator, and the puncture guide line G is displayed so as to be superimposed on the ultrasound image B on the basis of the set value.

What is claimed is:

1. An ultrasound diagnostic apparatus comprising:
   a vibrator array;
   a transmission circuit that transmits an ultrasound beam toward a subject from the vibrator array;
   a reception circuit that generates reception data by processing reception signals output from the vibrator array that has received an ultrasonic echo from the subject;
   an image producer that generates an ultrasound image on the basis of the reception data obtained by the reception circuit;
   a monitor that displays the ultrasound image generated by the image producer;
   a puncture needle to be inserted into the subject;
   an operating unit used to input an instruction from an operator; and
   a controller that selects either a live operation to display a puncture guide line so as to be superimposed on a real-time ultrasound image displayed on the monitor or a freeze operation to reproduce an ultrasound image of a predetermined frame on the monitor with the puncture guide line being superimposed on the monitor according to an operation through the operating unit by the operator, displays a partial puncture guide line composed from only both end portions of the puncture guide line with a middle portion of the puncture guide line being eliminated so as to be superimposed on the ultrasound image, when an instruction for non-display of the puncture guide line is given through the operating unit during the freeze operation, and automatically returns the eliminated middle portion of the puncture guide line and displays the puncture guide line including the middle portion entirely so as to be superimposed on the real-time ultrasound image without performing an operation to display the puncture guide line by the operator at the time of returning from the freeze operation to the live operation.

2. The ultrasound diagnostic apparatus according to claim 1,
   wherein the controller reproduces an ultrasound image of a frame before a predetermined time when non-display of the puncture guide line is instructed from the operating unit during the freeze operation.

3. The ultrasound diagnostic apparatus according to claim 1,
   wherein the controller performs loop reproduction of ultrasound images of a plurality of frames in a predetermined time range when non-display of the puncture guide line is instructed from the operating unit during the freeze operation.

4. The ultrasound diagnostic apparatus according to claim 1, further comprising:
   an image memory that stores an ultrasound image displayed during the freeze operation from which the middle portion of the puncture guide line has been eliminated according to an instruction from the operating unit.

5. The ultrasound diagnostic apparatus according to claim 2, further comprising:
   an image memory that stores an ultrasound image displayed during the freeze operation from which the middle portion of the puncture guide line has been eliminated according to an instruction from the operating unit.

6. The ultrasound diagnostic apparatus according to claim 3, further comprising:
   an image memory that stores an ultrasound image displayed during the freeze operation from which the middle portion of the puncture guide line has been eliminated according to an instruction from the operating unit.

7. The ultrasound diagnostic apparatus according to claim 1,
   wherein the controller changes a display color of the puncture guide line automatically at the time of switching from the live operation to the freeze operation.

8. The ultrasound diagnostic apparatus according to claim 1,
   wherein the controller changes a display color of the puncture guide line automatically at the time of switching from the live operation to the freeze operation.

9. The ultrasound diagnostic apparatus according to claim 3,
   wherein the controller changes a display color of the puncture guide line automatically at the time of switching from the live operation to the freeze operation.

10. An ultrasound image display method comprising:
    selecting and executing either a live operation to display a real-time ultrasound image on a monitor with a puncture guide line being superimposed on the monitor or a freeze operation to reproduce an ultrasound image of a predetermined frame on the monitor with the puncture guide line being superimposed on the monitor according to an operation of an operator; and
    displaying a partial puncture guide line composed from only both end portions of the puncture guide line with a middle portion of the puncture guide line being eliminated so as to be superimposed on the ultrasound image, when an instruction for non-display of the puncture guide line is given from the operator during the freeze operation, and automatically returning the eliminated middle portion of the puncture guide line and displaying the puncture guide line including the middle portion entirely so as to be superimposed on the real-time ultrasound image without performing an operation to display the puncture guide line by the operator at the time of returning from the freeze operation to the live operation.

11. The ultrasound diagnostic apparatus according to claim 1, wherein the controller eliminates only the middle portion of the puncture guide line, which has been displayed so as to be superimposed on the ultrasound image, while displaying a remaining portion other than the middle portion of the puncture guide line to thereby clearly display body tissue and a puncture needle located in the middle portion of the ultrasound image.

12. The ultrasound diagnostic apparatus according to claim 1, wherein the controller eliminates only the middle portion of the puncture guide line, which has been displayed so as to be superimposed on the ultrasound image, while displaying a remaining portion other than the middle portion of the puncture guide line to thereby acquire information from the puncture guide line.

\* \* \* \* \*